(12) United States Patent
Cornwall et al.

(10) Patent No.: US 7,074,239 B1
(45) Date of Patent: *Jul. 11, 2006

(54) RESORBABLE POSTERIOR SPINAL FUSION SYSTEM

(75) Inventors: G. Bryan Cornwall, San Diego, CA (US); Gary Sohngen, San Pedro, CA (US); Joseph M. Lane, New York, NY (US); Emre A. Tomin, New York, NY (US)

(73) Assignee: Cytori Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/793,155

(22) Filed: Mar. 3, 2004

Related U.S. Application Data

(63) Continuation of application No. 10/132,623, filed on Apr. 25, 2002, now Pat. No. 6,719,795.

(60) Provisional application No. 60/286,613, filed on Apr. 25, 2001.

(51) Int. Cl.
*A61F 2/44* (2006.01)

(52) U.S. Cl. .................. 623/17.11; 623/17.16; 606/61

(58) Field of Classification Search ............ 623/17.11, 623/1.16, 23.75, 17.16, 17.15, 17.12; 606/10, 606/61, 69, 70, 77
See application file for complete search history.

(56) References Cited

U.S. PATENT DOCUMENTS

| 5,026,373 | A | * | 6/1991 | Ray et al. ................ 606/61 |
| 5,116,334 | A | * | 5/1992 | Cozad et al. .............. 606/61 |
| 5,147,402 | A | * | 9/1992 | Bohler et al. .......... 623/16.11 |
| 5,391,168 | A | * | 2/1995 | Sanders et al. ............ 606/61 |
| 5,437,672 | A | * | 8/1995 | Alleyne ................... 606/61 |
| 5,755,781 | A | * | 5/1998 | Jayaraman ............. 623/1.16 |
| 5,902,332 | A | * | 5/1999 | Schatz .................. 623/1.16 |
| 5,980,540 | A | * | 11/1999 | Bruce ................... 606/151 |
| 6,248,107 | B1 | * | 6/2001 | Foley et al. .............. 606/61 |
| 6,332,895 | B1 | * | 12/2001 | Suddaby ............... 623/17.11 |
| 6,336,930 | B1 | * | 1/2002 | Stalcup et al. ............ 606/69 |
| 6,364,883 | B1 | * | 4/2002 | Santilli .................. 606/69 |
| 6,432,108 | B1 | * | 8/2002 | Burgess et al. ........... 606/61 |
| 6,641,585 | B1 | * | 11/2003 | Sato et al. ................ 606/61 |
| 6,641,586 | B1 | * | 11/2003 | Varieur ................... 606/61 |
| 6,719,795 | B1 | * | 4/2004 | Cornwall et al. ....... 623/17.11 |
| 2001/0014826 | A1 | * | 8/2001 | Biedermann et al. ... 623/17.11 |
| 2002/0040222 | A1 | * | 4/2002 | Hashimoto et al. ........ 606/61 |
| 2002/0040223 | A1 | * | 4/2002 | Sato et al. ................ 606/61 |
| 2003/0004573 | A1 | * | 1/2003 | Bagby .................. 623/17.11 |
| 2003/0083746 | A1 | * | 5/2003 | Kuslich ................ 623/17.11 |

* cited by examiner

*Primary Examiner*—Pedro Philogene
(74) *Attorney, Agent, or Firm*—Stout, Uxa, Buyan & Mullins, LLP

(57) ABSTRACT

Rolled resorbable membranes and methods for their application have been discovered. In accordance with one aspect of the present invention, rolled resorbable membranes are applied to the transverse processes of two or more vertebrae to facilitate fusion of the vertebrae.

23 Claims, 5 Drawing Sheets

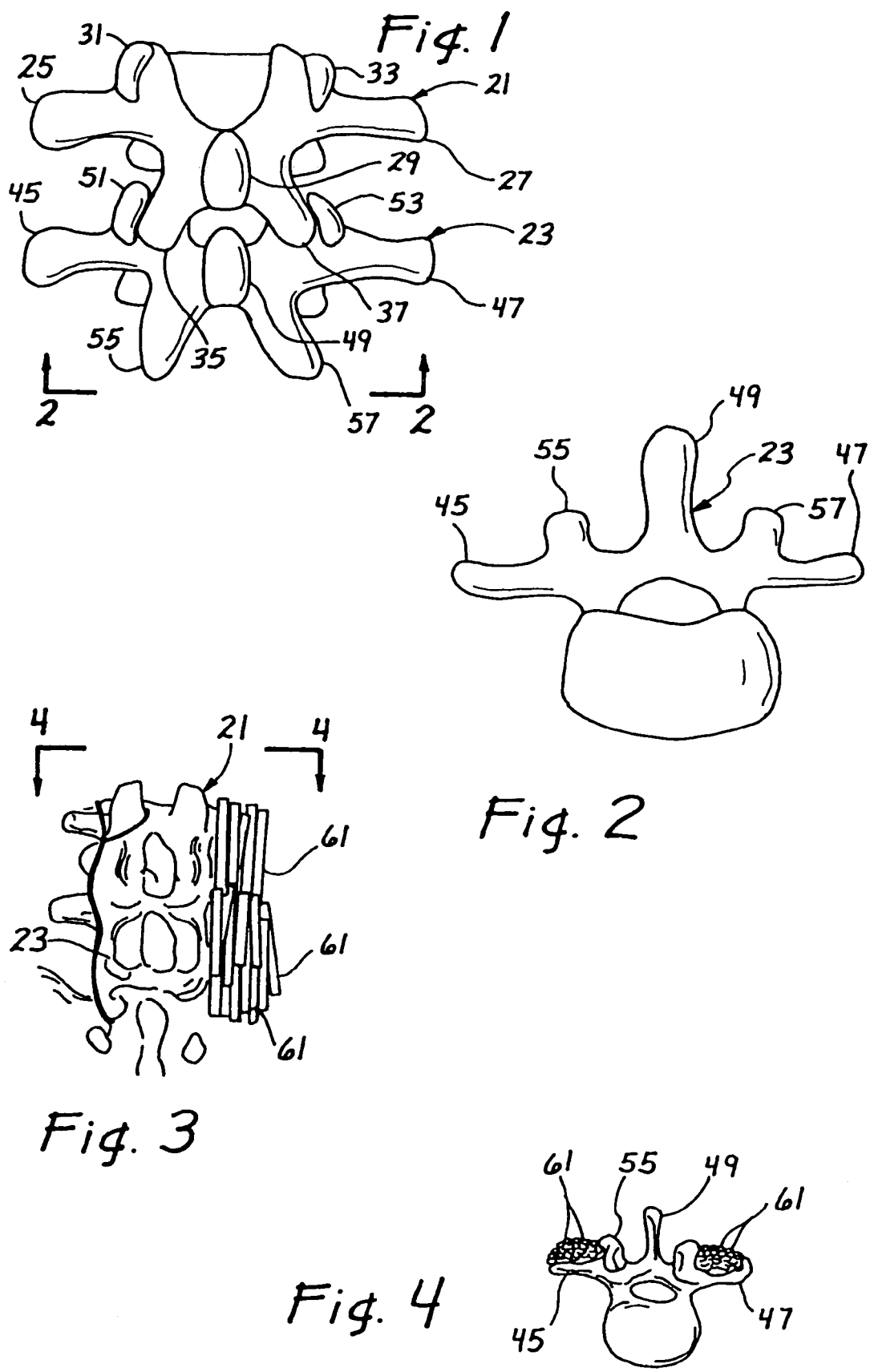

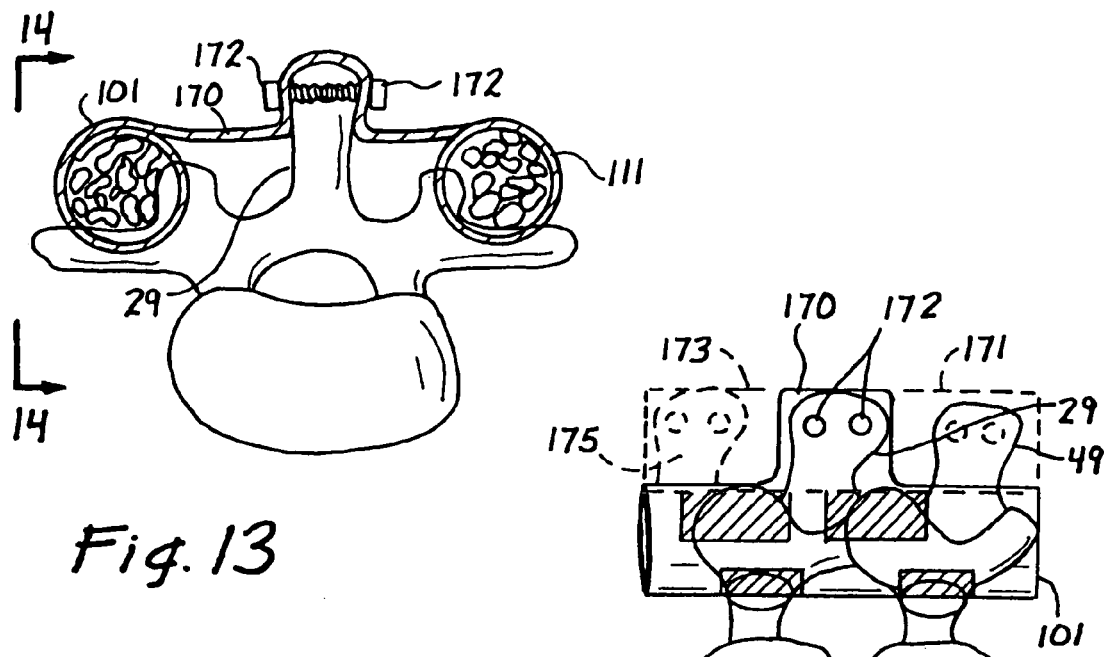
Fig. 13
Fig. 14
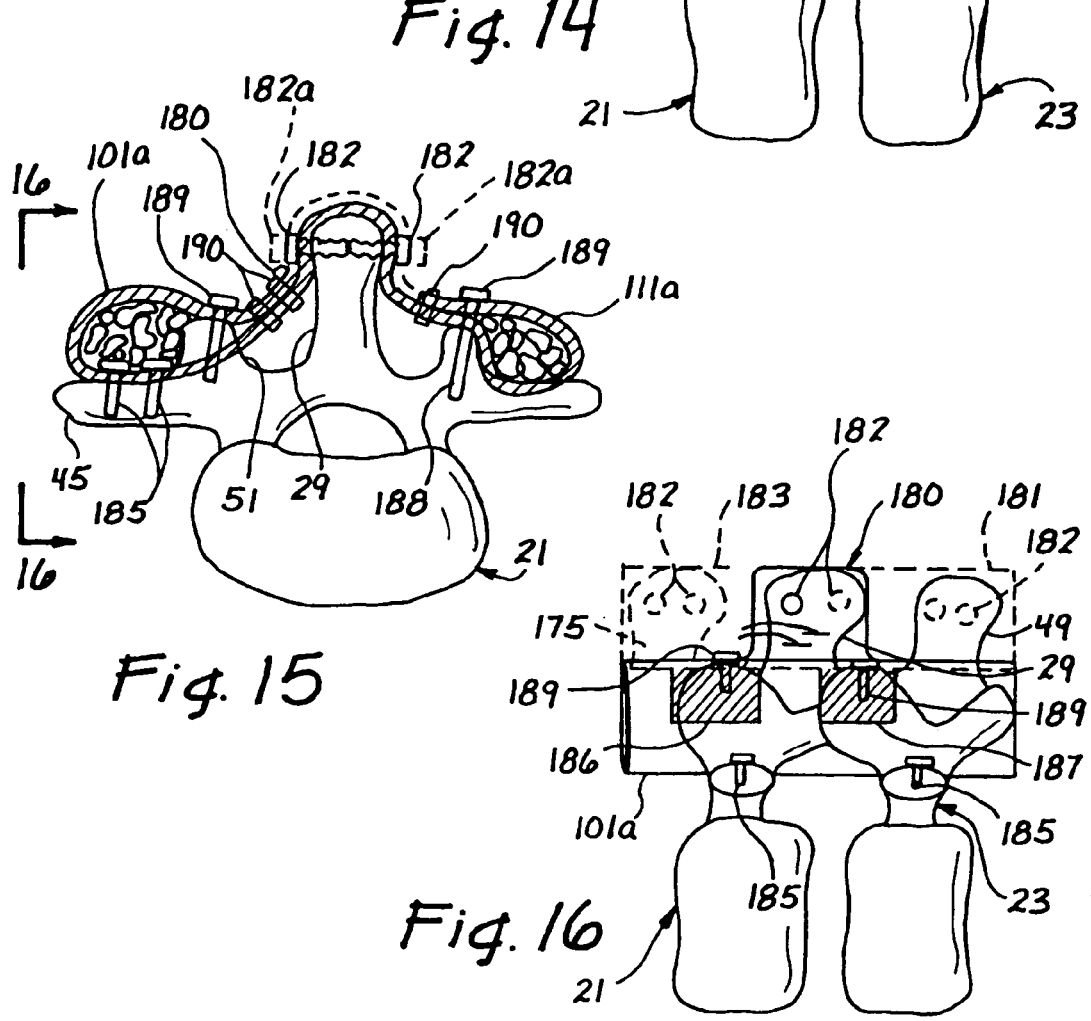
Fig. 15
Fig. 16

RESORBABLE POSTERIOR SPINAL FUSION SYSTEM

CROSS-REFERENCE TO RELATED APPLICATIONS

This application is a continuation of application Ser. No. 10/132,623 filed Apr. 25, 2002 now U.S. Pat. No. 6,719,795 and claims priority to provisional application, U.S. Application No. 60/286,613, filed Apr. 25, 2001, the entire contents of which are hereby incorporated by reference.

BACKGROUND OF THE INVENTION

1. Field of the Invention

The present invention relates to medical implants and, more particularly, to medical implants for the correction of an unstable parts of the spine by joining two or more vertebrae.

2. Description of Related Art

Back pain remains a major public health problem, especially among aged people. Persistent and severe back pain often causes debility and disability, and this pain is closely associated with intervertebral disc abnormalities of the spine.

The human spine is a flexible structure comprised of thirty-three vertebrae. Intervertebral discs separate and cushion adjacent vertebrae, act as shock absorbers, and allow bending between the vertebrae. An intervertebral disc comprises two major components: the nucleus pulposus and the annulus fibrosis. The nucleus pulposus is centrally located in the disc and occupies 25–40% of the disc's total cross-sectional area. The annulus fibrosis surrounds the nucleus pulposus and resist torsional and bending force applied to the disc. Vertebral end-plates separate the disc from the vertebrae on either side of the disc.

As a result of exertion, injury, illness, accident or abuse, one or more of the vertebrae and/or one or more discs may become damaged and malfunctional. Specifically, disorders of the vertebrae and discs include but are not limited to 1) disruption of the disc annulus such as annular fissures; 2) chronic inflammation of the disc; 3) localized disc herniations with contained or escaped extrusions; and 4) relative instability of the vertebrae surrounding the disc.

Various approaches have been developed to treat back pain. Minor back pain can be treated with medication and other non-invasive therapy. However, it is often necessary to remove at least a portion of the damaged and/or malfunctioning back component. For example, when a disc becomes ruptured, a discectomy surgical procedure can be performed to remove the ruptured disc and to fuse the two vertebrae between the removed disc together.

Spinal fusion is indicated to provide stabilization of the spinal column for disorders such as structural deformity, traumatic instability, degenerative instability, and post resection iatrogenic instability. Fusion, or arthrodesis, can thus be achieved, for example, by the formation of an osseous bridge between adjacent motion segments. The fusion can be accomplished either anteriorly between contiguous vertebral bodies or posteriorly between consecutive transverse processes, laminae or other posterior aspects of the vertebrae. Typically, the osseous bridge, or fusion mass, is biologically produced by recreating conditions of skeletal injury along a "fusion site" and allowing the normal bone healing response to occur. This biologic environment at a proposed fusion site requires the presence of osteogenic or osteopotential cells, adequate blood supply, sufficient inflammatory response, and appropriate preparation of local bone. To this end, a process known as decortication is typically used to prepare bone and increase the likelihood of fusion. Decortication involves removing the outer cortex of spinal bone with a burr to induce bleeding bone and release bone marrow. Decortication also initiates the inflammatory response, releases osteoinductive cytokines, provides additional osteogenic cells, and creates a host attachment site for the subsequent fusion mass. Bone graft materials are often used to promote spinal fusions. Autogenous iliac crest cortico-cancellous bone is presently a widely-used bone grafting material.

FIG. 1 illustrates two adjacent vertebrae 21 and 23 of a human spine. The first vertebra 21 comprises left and right transverse processes 25 and 27, respectively, and further comprises a first spinous process 29. The first vertebra 21 further comprises left and right superior articular processes 31 and 33, respectively, and comprises left and right inferior articular processes 35 and 37, respectively. Similarly, the second vertebra 23 comprises left and right transverse processes 45 and 47, respectively, and further comprises a second spinous process 49. The second vertebra 23 further comprises left and right superior articular processes 51 and 53, respectively, and comprises left and right inferior articular processes 55 and 57, respectively. A cross-sectional view of the vertebrae 23, taken along the line 2—2 of FIG. 1, is shown in FIG. 2.

In FIG. 3 an autogenous iliac crest cortico-cancellous bone is grafted onto the two spinous processes 27 and 47 of the two vertebrae 21 and 23. Donor cortical bone from the iliac crest is cut into small rectangular grafts 61 which are placed over the partially-decorticated spinus processes 27 and 47. Donor cancellous bone from the iliac crest is placed between the rectangular grafts 61 and the spinus processes 27 and 47. This autograft process has a shortcoming, however, because of the additional surgery that is required to harvest the autogenous donor materials. The additional surgery can increase the risk of infection and can reduce structural integrity at the donor site. Furthermore, many patients complain of significant pain for several years after the surgery.

In early spinal fusion techniques, bone material, or bone osteogenic fusion devices, were simply disposed between adjacent vertebrae, typically at the posterior aspect of the vertebrae. In the early history of these osteogenic fusion devices, the osteogenic fusion devices were formed of cortical-cancellous bone. Consequently, the spine was stabilized by way of screws, plates and/or rods spanning the affected vertebrae. With this technique, once fusion occurred across and incorporating the bone osteogenic fusion device, the hardware used to maintain the stability of the spine became superfluous.

Following the successes of the early fusion techniques, focus was directed to modifying the device placed within the intervertebral space to support and fuse together adjacent vertebrae by posterior-fusion or anterior grafting. For example, surgical prosthetic implants for vertebrae described in U.S. Pat. No. 5,827,328 include rigid annular plugs that have ridged faces to engage adjacent vertebrae to resist displacement and allow ingrowth of blood capillaries and packing of bone graft. These annular implants are usually made of biocompatible carbon fiber reinforced polymers, or traditional orthopaedic implant materials such as nickel, chromium, cobalt, stainless steel or titanium. The individual implants are internally grooved and are stacked against each other to form a unit between the two adjacent vertebrae.

Another intervertebral fusion device described by Kozak et al. (U.S. Pat. No. 5,397,364) includes an assembly of two lateral spacers and two central spacers, which defines a channel in the center of the fusion device for insertion of bone graft material. The spacers are maintained in their configuration within the intradiscal space by screws threaded into a vertebra from the outside of the disc.

Cylindrical hollow implants or "cages" are represented by the patents to Bagby, U.S. Pat. No. 4,501,269; Brantigan, U.S. Pat. No. 4,878,915; Ray, U.S. Pat. No. 4,961,740; and Michelson, U.S. Pat. No. 5,015,247. The outer wall of the cage creates an interior space within the cylindrical implant that is filled with bone chips, for example, or other bone growth-inducing material. The cylindrical implant can include a threaded exterior to permit threaded insertion into a tapped bore formed in the adjacent vertebrae. One fusion cage implant is disclosed in U.S. Pat. No. 5,026,373 to Ray et al. The Ray '373 fusion cage includes apertures extending through its wall which communicate with an internal cavity of the cage body. The adjacent vertebral bone structures communicate through the apertures with bone growth inducing substances within the internal cavity to unite and eventually form a solid fusion of the adjacent vertebrae. Other prosthetic implants are disclosed in U.S. Pat. Nos. 4,501,269, 4,961,740, 5,015,247 and 5,489,307. Other fusion implants have been designed to be impacted into the intradiscal space.

Experience over the last several years with these interbody fusion devices has demonstrated the efficacy of these implants in yielding a solid fusion. Variations in the design of the implants have accounted for improvements in stabilizing the motion segment while fusion occurs. Nevertheless, some of the interbody fusion devices still have difficulty in achieving a complete fusion, at least without the aid of some additional stabilizing device, such as a rod or plate. Moreover, some of the devices are not structurally strong enough to support the heavy loads and bending moments applied at certain levels of the spine, namely those in the lumbar spine.

Even with devices that do not have these difficulties, other less desirable characteristics exist. Recent studies have suggested that the interbody fusion implant devices, or cages as they are frequently called, lead to stress-shielding of the bone within the cage. It is well known that bone growth is enhanced by stressing or loading the bone material. The stress-shielding phenomenon relieves some or all of the load applied to the material to be fused, which can greatly increase the time for complete bone growth, or disturb the quality and density of the ultimately formed fusion mass. In some instances, stress-shielding can cause the bone chips or fusion mass contained within the fusion cage to resorb or evolve into fibrous tissue rather than into a bony fusion mass.

A further difficulty encountered with many fusion implants is that the material of the implant is not radiolucent. Most fusion cages are formed of metal, such as stainless steel, titanium or porous tantalum. The metal of the cage shows up prominently in any radiograph (x-ray) or CT scan. Since most fusion devices completely surround and contain the bone graft material housed within the cage, the developing fusion mass within the metal cage between the adjacent vertebrae cannot be seen under traditional radiographic visualizing techniques and only with the presence of image scatter with CT scans. Thus, the spinal surgeon does not have a means to determine the progress of the fusion, and in some cases cannot ascertain whether the fusion was complete and successful.

The field of spinal fusion can be benefited by an intervertebral fusion device that beneficially attenuates or eliminates the risk of stress-shielding of the fusion mass, and that also provides for visualization of the fusion mass as the arthrodesis progresses.

SUMMARY OF THE INVENTION

Rolled resorbable membranes and methods for their application have been discovered. In accordance with one aspect of the present invention, rolled resorbable resorbable membranes are applied to the transverse processes of two or more vertebrae to facilitate fusion of the vertebrae.

BRIEF DESCRIPTION OF THE DRAWINGS

FIG. 1 illustrates two adjacent vertebrae of a human spine in accordance with the prior art;

FIG. 2 is an end view of the two vertebrae of FIG. 1;

FIG. 3 illustrates an posterior lateral fusion of the two vertebrae of FIG. 1 using bone grafts;

FIG. 4 is an end view of the two vertebrae of FIG. 3;

FIG. 13 illustrates two rolled resorbable membranes secured onto two vertebrae with screws, for facilitating posterior lateral fusion of the vertebrae in accordance with another alternative embodiment of the present invention;

FIG. 14 is a side elevation view of the posterior lateral fusion configuration of FIG. 13 in accordance with an alternative embodiment of the present invention;

FIG. 13 illustrates two rolled resorbable membranes secured onto two vertebrae with screws, for facilitating posterior lateral fusion of the vertebrae in accordance with an alternative embodiment of the present invention;

FIG. 14 is a side elevation view of the posterior lateral fusion configuration of FIG. 13 in accordance with the present invention;

FIG. 15 illustrates two resorbable membranes secured onto two vertebrae with screws, for facilitating posterior lateral fusion of the vertebrae in accordance with an another alternative embodiment of the present invention;

FIG. 16 is a side elevation view of the posterior lateral fusion configuration of FIG. 13 in accordance with the present invention;

DETAILED DESCRIPTION OF THE PRESENTLY PREFERRED EMBODIMENTS

Figure 5:
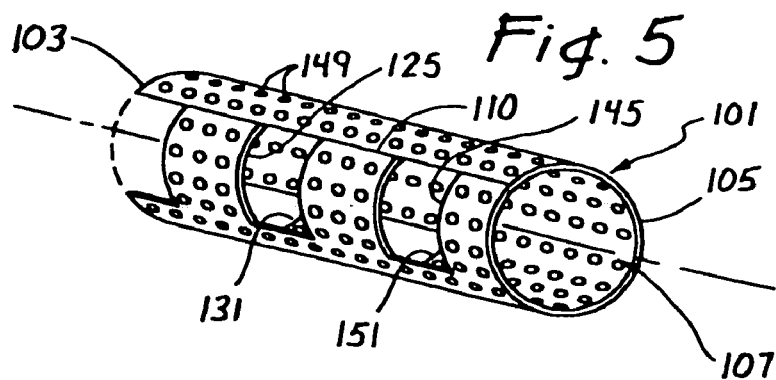
FIG. 5 illustrates a rolled resorbable membrane for facilitating posterior lateral fusion of two vertebrae in accordance with the present invention.

Turning to FIG. 5, a rolled resorbable membrane 101 is shown for facilitating posterior lateral fusion of at least two vertebrae. The rolled resorbable membrane 101 is sized and shaped to be placed into contact with at least two adjacent vertebrae and to facilitate osteogenic fusion between the vertebrae. As presently embodied, the rolled resorbable membrane 101 comprises a first end 103, a second end 105, and an axis 107 extending between the first end 103 and the second end 105. A lumen 107 extends along the length of the axis 107 between the first end 103 and the second end 105.

In the illustrated embodiment, the rolled resorbable membrane 101 is formed into a cylindrical shape wherein the first end 103 and the second end 105 are open to the lumen 107. This cylindrical shape may be achieved by providing a planar resorbable membrane and bringing two opposing edges together. In the embodiment of FIG. 5, a planar, rectangular resorbable membrane with four edges is wrapped around a mandrel to bring two opposing edges of the rectangular resorbable membrane into close proximity of one another. The two edges are then secured together by, for example, sutures, heat welding (discussed, infra), or staples. The resorbable membranes of the present invention may comprise other perimeters besides rectangular perimeters.

As presently embodied, the rectangular resorbable membrane 101 is brought to a glass transition temperature either before or after being wrapped around the mandrel and, subsequently, allowed to cool while still formed around the mandrel. After the resorbable membrane 101 has cooled to a temperature below the glass transition temperature, the rolled resorbable membrane 101 is removed from the mandrel to thereby yield a rolled resorbable membrane 101 in the cylindrical shape of the mandrel. Although the mandrel used to form the resorbable membrane 101 preferably has a cylindrical cross section, other cross sections, such as, for example, oval cross sections may be used. The cross sectional shapes and/or areas may vary along the length of the axis 107 in modified embodiments. For example, a resorbable membrane 101 may be rolled to have a slightly conical or hour glass shape. Moreover, the resorbable membrane 101 may be rolled around another object or, alternatively, may be rolled without the use of any forming structure. For example, the resorbable membrane 101 may be placed into heated saline solution, rolled, and subsequently lifted out of the heated saline solution and allowed to cool in the rolled configuration.

In the illustrated embodiment of FIG. 5, the two opposing edges of the rectangular resorbable membrane 101 are brought together around the mandrel to form a seam 110. The seam 110 adds flexibility and to the rolled resorbable membrane 101, so that, for example, the rolled resorbable membrane 101 may be shaped, with or without heating, to have an rectangular, oval, triangular or other cross section. For example, a mandrel with a rounded-corner triangular shape may be used to shape a planar sheet to have an approximately triangular cross section. FIG. 15, discussed infra, illustrates a rolled resorbable membrane having a somewhat triangular cross section which facilitates an attenuated radial protrusion of the rolled resorbable membrane away from the vertebrae. One or both of the two opposing edges of the resorbable membrane 101 may need to be trimmed so that a smooth seam 110 is generated. In modified embodiments, the seam 110 may comprise a slight or substantial overlap of one of the two edges of the resorbable membrane 101 over the other edge. This overlap may span a length of, for example, which is equal to a radius or even a diameter of the resorbable membrane 101. In other words, the overlap may span an arc length of between 1 and approximately 180 degrees. In modified embodiments, the overlap may be even greater. The overlapping edge may completely encircle the resorbable membrane 101 one or more times, for example, for added strength. In modified embodiments, the opposing edges may not contact one another at all, so that a gap is formed therebetween. The gap is preferably relatively small, spanning an arch length of about 1 to about 45 degrees and, more preferably, an arch length of about 1 to 15 degrees. Preferably, the gap should not be so large as to impede the function of the resorbable membrane 101 of containing bone grafts or bone graft substitutes.

The amount of overlap, and any gap size, may vary along the length of the axis 107. For example, gaps may be formed at certain locations at the seam 110 to accommodate transverse or articular processes, laminae or other posterior aspects of the vertebrae, and overlaps may be formed between the gaps for reinforcement. In accordance with one aspect of the present invention, the seam 110 is disposed at a boundary of at least one window of the rolled resorbable membrane 101. The illustrated embodiment of FIG. 5 shows a rolled resorbable membrane 101 having a first lateral window 125 and a second lateral window 145 disposed therein, with the seam 110 being disposed adjacent to both the first lateral window 125 and the second lateral window 145. In embodiments with fewer or greater lateral windows, the seam 110 may be disposed adjacent to one or more of the lateral windows. Moreover, in modified embodiments, the seam 110 may be disposed adjacent to one or more articular windows. For example, the seam 110 may be disposed adjacent to one or both of the first articular window 131 and the second articular window 151 illustrated in FIG. 5. The seam 110 may comprise a straight, curved, or other line, and may extend fully, partially, or intermittently along the length of the rolled resorbable membrane 101. In modified embodiments, the seam may be disposed adjacent to at least one lateral window and at least one articular window. In other modified embodiments, the seam may be omitted altogether.

Various means for attaching the rolled resorbable membrane 101 to spinal elements are contemplated. For example, the rolled resorbable membrane 101 is preferably secured via the spinal elements, e.g., transverse and superior articular processes, contacting the rolled resorbable membrane and, more preferably, fitting into windows of the rolled resorbable membrane 101. Adjacent tissues preferably press at least portions of the rolled resorbable membrane 101, or windows thereof, into proximity of or over the spinal elements. Sutures or staples may be used to attach the membrane to the paravertebral muscle. As another example, portions of the rolled resorbable membrane may be secured to the vertebrae bone using resorbable bone screws or tacks. Tucking or folding of portions of the rolled resorbable membrane 101 into anatomical crevices or about spinal elements may be sufficient to fix its position in other embodiments. An adhesive such as a fibrin sealant, or a resorbable cyanoacrylate adhesive may further be utilized to secure the rolled resorbable membranes 101, alone or in combination with the above means of attachment.

In accordance with one aspect of the present invention, one or more portions of the rolled resorbable membrane 101 can be heat bonded, such as with a bipolar electro-cautery device, ultrasonically welded, or similarly sealed directly to one or more spinal elements. Such a device can be used to heat the barrier membrane at various locations, such as at the edges and at points in the therebetween, at least above its glass transition temperature, and preferably above its softening point temperature. The glass transition temperature of the preferred material (70:30 poly L-lactide-co-D, L-lactide (PLDLA)) is about 55° Celsius, while its softening point temperature is above 110° Celsius. The material is heated along with adjacent bone tissue such that the two components bond together at their interface. In another embodiment, the rolled resorbable membrane 101 can be heat bonded or sealed directly to itself such as, for example, at the seam 110, and/or to muscle or other adjacent soft tissue, for example. For example, the rolled resorbable membrane may be formed into a cylinder in vitro, or wrapped around a spinal element in vivo, and then heat joined to itself. Moreover, the technique of heat-sealing the rolled resorbable membrane 101 material to itself and/or to body tissue may be combined with another attachment method for enhanced anchoring. For example, the rolled resorbable membrane 101 material may be temporarily affixed in position using two or more points of heat sealing (i.e., heat welding) using an electro-cautery device, and sutures, staples or glue can then be added to secure the barrier membrane into place. The seam 110 may them be heat welded to itself or, alternatively, formed to slightly overlap itself without any heat welding at the seam 110 for added flexibility of the rolled resorbable membrane.

The rolled resorbable membrane 101 is formed with pores 149 in accordance with a preferred embodiment of the present invention. As presently embodied, the pores 149 within the rolled resorbable membrane 101 are both cell and fluid permeable, and the base material of the rolled resorbable membrane 101 is rigid enough to maintain an available space, e.g., lumen, within the rolled resorbable membrane 101 along a length of the rolled resorbable membrane 101 between, for example, the first vertebra 21 and the second vertebrae 23 for ideal bone regeneration. In the illustrated embodiment, an available space, for the formation of bone, is maintained within the rolled resorbable membrane 101 along a length of the rolled resorbable membrane 101 between the right transverse process 27 of the first vertebra 21 and the right transverse process 27 of the second vertebra 23. Additionally, the base material 44 is resorbable, according to the presently preferred embodiment.

It is recognized by the present invention that mesenchymal stem cells, which can be found in surrounding mesodermal tissues, are the precursor cells which eventually form muscle, cartilage, tendons, ligaments, connective tissues, and bone. These cells are present in these tissues and are involved in the perpetual renewal of each specific tissue, although in their earliest stage of development, these cells are not committed to becoming any given tissue. An uncommitted mesenchymal stem cell found in muscle, for example, will not strictly become a muscle cell. If the mesenchymal stem cell is needed to become a bone cell, the mesenchymal stem cell may migrate to a bone defect and differentiate into a bone forming cell.

The mechanism for attracting these cells, and for directing them to become specific tissue cells, can be controlled by morphogenic proteins and/or other factors. In bone, for example, these proteins are commonly referred to as bone morphogenic proteins. The pores 149 of the rolled resorbable membrane 101 harness this mechanism, by allowing, for example, bone morphogenic proteins from within the protected space of the rolled resorbable membrane 101 to attract mesenchymal stem cells from the surrounding connective tissues, musculature, periosteum, and/or vasculature. The bone morphogenic proteins, for example, are supplied from bone grafts, bone graft substitutes or other substances disposed within the protected space of the rolled resorbable membrane 101, and are further supplied the at least partially decorticated transverse processes and/or articular processes which are exposed to the protected space of the rolled resorbable membrane 101 via windows within the rolled resorbable membrane 101. The attracted elements are then directed to differentiate into bone forming cells, which are essential for new bone formation on the at least partially decorticated transverse processes and/or articular processes and otherwise within the protected space of the rolled resorbable membrane 101.

In addition, the pores 149 of the present invention allow vital contributions of blood vessels from surrounding tissues, musculature, and periosteum into the protected space of the rolled resorbable membrane 101. Blood vessels invading the protected space within the rolled resorbable membrane 101 of the present invention greatly enhance the generation of new bone, as compared to cell-occlusive membranes which limit the supply of blood to that coming from within the protected space itself. The ability for capillaries from surrounding soft tissues to proliferate into the protected space of the rolled resorbable membrane 101 may help prevent migrating cells from the osseous bed and the periosteum from outstripping their proliferating blood supply. This proliferation of blood vessels increases the potential of spontaneous bone regeneration within the protected space of the rolled resorbable membrane 101. Furthermore, mesenchymal stem cells are believed to be perivascular (around blood vessels) connective tissue cells, which would additionally foster bone regeneration by the transmembranous sprouting of capillaries, since most vasculature has associated connective tissues. In modified embodiments, non-cell permeable pores may be used or no pores altogether, in which case cells and vasculature could still proliferate into the protected space of the rolled resorbable membrane 101 through the opposing open ends of the rolled resorbable membrane 101.

As presently embodied, the rolled resorbable membrane 101 comprises either a biodegradable synthetic material or a biodegradable natural material, or both. The biodegradable synthetic material may comprise polymers, for example, and the biodegradable natural material may comprise collagen, for example. Each of the pores 149 preferably has a diameter within a range of between 20 microns and 3000 microns. In the presently preferred embodiment, each aperture 46 comprises a diameter of approximately 1500 microns. A thickness of the base material 44 is preferably within a range between 0.25 mm and 3 mm, and, more preferably, between 0.5 mm and 2 mm. The base material of the rolled resorbable membrane 101 may also be configured with greater or smaller thicknesses in modified embodiments. The pattern of distribution of the pores 149 may vary according to the dimensions and characteristics of the bone defect, e.g. spinal fusion environment.

The ranges of pore 149 sizes, base material thickness, and pore 149 shapes and distributions are preferably implemented by the present invention in order to optimize the rolled resorbable membrane 101 to different environmental conditions. Examples of the different environmental conditions encountered in different bone defects include the location of the defect, the type of defect, size of the defect, the presence or absence of periosteum, and the general condition of the adjacent soft tissues covering the bone defect.

In a preferred embodiment of the present invention, the rolled resorbable membrane 101 comprises a base material of poly lactide polymer or co-polymer and, more preferably, comprises 70:30 poly L-lactide-co-D, L-lactide (PLDLA). As presently embodied, the material comprises poly (L-lactide-co-D,L-lactide) 70:30 Resomer LR708, which may be manufactured and supplied from Boehringer Ingelheim KG of Germany. A pre-formed planar membrane made from PLA can be shaped at the time of surgery into a cylinder by bringing the material to its glass transition temperature, using heating iron, hot air, heated sponge or hot water bath methods. The base material of the rolled resorbable membrane 101, according to the present invention, may be impregnated with a variety of substances for promoting the regeneration of different tissues such as bone and blood vessels. The base material may be impregnated with a chemotactic substance for influencing cell-migration, an inhibitory substance for influencing cell-migration, a mitogenic growth factor for influencing cell proliferation and a growth factor for influencing cell differentiation (e.g. insulinelike growth factor, transforming growth factor-beta, fibroblast growth factor, platelet-derived growth factor), and factors which promote neoangiogenesis (formation of new blood vessels).

The protected space of the rolled resorbable membrane is preferably filled with bone grafts or bone graft substitutes. The multiple bone graft fragments, for example, would naturally be dispersed and resorbed unless they can be rigidly held together and provided with sufficient blood supply. The rolled resorbable membrane of the present invention, in addressing the fact that bone fragment resorption can present a significant obstacle to efficient healing and bone formation, provides a protected-space structure for holding bone grafts or other substitutes rigidly together while, at the same time, providing for optimal blood supply to the protected space. Moreover, in accordance with the present invention, a medium, e.g., a sponge, for carrying bioactive substances to regulate the complex cascade of cellular events of bone repair, may be implanted into the protected space of the rolled resorbable membrane in addition to or as an alternative to bone grafts or other bone graft substitutes. Such a bioactive substance may comprise a bone morphogenic protein (BMP) for use as an alternative or adjunctive bone graft material.

The bone morphogenic protein preferably comprises an osteoinductive cytokine extracted from bone matrix that is capable of inducing bone formation when implanted in a fracture or surgical bone-formation site. The term BMP preferably refers to a group of bone morphogenic proteins belong to the TGF-.beta. super family. The structures of eleven proteins, BMP-1 through BMP-11 have been elucidated. Recombinantly produced human bone morphogenetic protein-2 (rhBMP-2) has been demonstrated in several animal models to be effective in regenerating bone in skeletal defects. The following events are believed to occur when BMPs are applied to a bony site: Osteogenic and chondrogenic precursor cells accumulate, cartilage forms and matures, and vascularization occurs during bone formation. As bone formation proceeds, the cartilage and carrier are resorbed. The final result is the restoration of bone and bone marrow in the protected space or defect site. The purification of bovine bone-derived bone-inductive protein (Wang et al. 1988) led to the cloning of recombinant human (rh) BMP-2 through rhBMP-8 (Wozney et al. 1988; Wozney 1989; Celeste et al. 1990; Celeste et al. 1992). BMP-2 through BMP-8 are related proteins with several common characteristics. Each BMP can be synthesized in a precursor form, with a hydrophobic secretory leader sequence and a substantial propeptide region. The mature protein can consists of a dimer of the carboxy-terminal portion of the propeptide molecule. All of the mature regions of these rhBMPs may contain one or more N-linked glycosylation sites and seven cysteine residues. The locations of the cysteine residues may be conserved within all members of this gene family. These BMPs may prove particularly useful in spinal-fusion surgeries such as disclosed herein for promoting osteogenic formation and healing.

Figure 6:
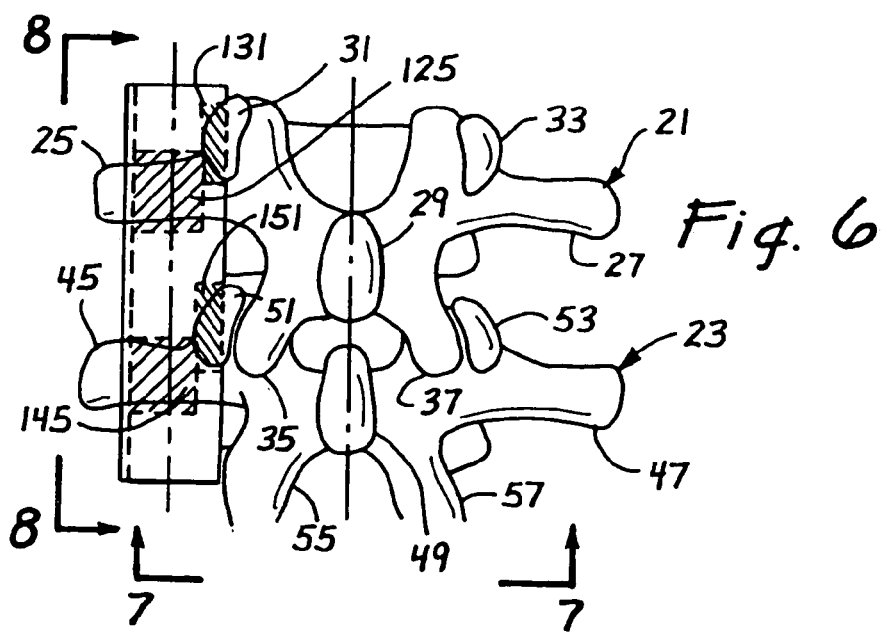
FIG. 6 illustrates a rolled resorbable membrane placed onto two vertebrae for facilitating posterior lateral fusion of the vertebrae in accordance with the present invention.
Figure 7:
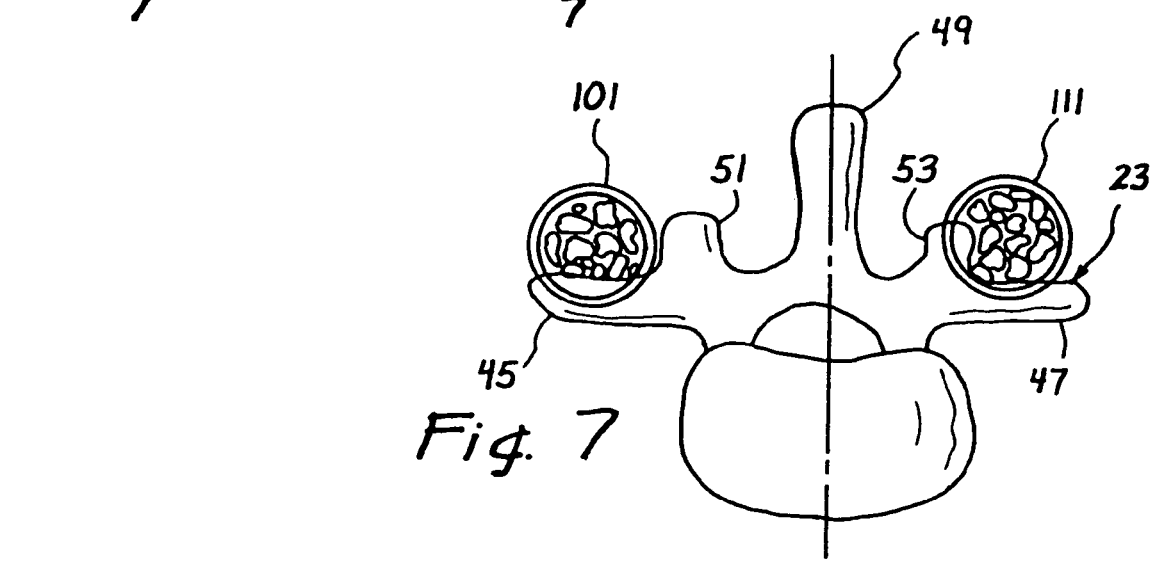
FIG. 7 is an end view of the posterior lateral fusion configuration of FIG. 6 in accordance with the present invention.
Figure 8:
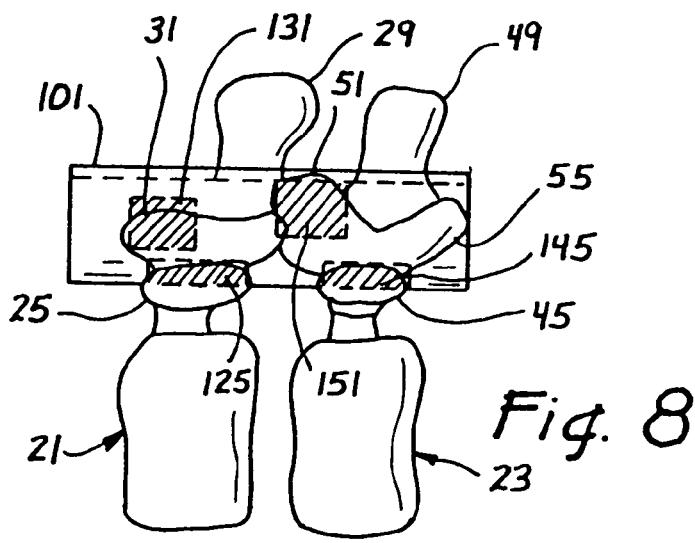
FIG. 8 is a side elevation view of the posterior lateral fusion configuration of FIG. 6 in accordance with the present invention.

In FIG. 6, a rolled resorbable membrane 101 is fitted onto the spinal elements of a first vertebra 21 and a second vertebra 23. More particularly, in the illustrated embodiment of FIG. 6, the rolled resorbable membrane 101 is secured to a left transverse process 25 of the first vertebra 21 via a first lateral window 125 and is secured to a left transverse process 45 via a second lateral window 145. In accordance with one embodiment of the present invention, the rolled resorbable membrane 101 is secured to the first vertebra 21 and the second vertebra 23 via only the first lateral window 125 and the second lateral window 145. The left transverse process 45 and the left transverse process 45 are preferably decorticated on the surfaces thereof that align with the first lateral window 125 and the second lateral window 145. The sizes and shapes of the decorticated surfaces may correspond to the sizes and shapes of the corresponding windows, or may be smaller or, more preferably, larger than the sizes and shapes of the corresponding windows. In one embodiment, at least one of the left transverse process 25 and the left transverse process 45 protrudes at least partially through at least one of the first lateral window 125 and the second lateral window 145, respectively. The portions of the left transverse process 25 and the left transverse process 45 that protrude into the protected space of the rolled resorbable membrane 101, via the first lateral window 125 and the second lateral window 145, are preferably decorticated to promote osteogenesis within the protected space of the rolled resorbable membrane 101. For example, bone grafts, bone graft substitutes and/or BMP-loaded or soaked collagen sponges can be placed within the protected space of the rolled resorbable membrane 101 and in contact with the decorticated portions of the left transverse process 25 and the left transverse process 45. Vasculature and cell structure will permeate through the rolled resorbable membrane 101 via the pores 149, portions of the windows 125, 145, and the open, opposing ends 103, 105 to thereby promote the formation of bone within the protected space of the rolled resorbable membrane 101. The rolled resorbable membrane 101 will eventually be resorbed, leaving a cylindrical bone formation fusing together the left transverse process 25 and the left transverse process 45 in accordance with the illustrated embodiment. In the presently preferred embodiment, another rolled resorbable membrane 111 is formed in a similar way on the right transverse process 27 of the first vertebra 21 and the right transverse process 47 of the second vertebra 23, as shown in the end view of FIG. 7. However, in other embodiments only a single rolled resorbable membrane is used as illustrated in FIG. 6. A side elevational view of the rolled resorbable membrane 101 fitted onto the first vertebra 21 and the second vertebra 23 is shown in FIG. 8. The end view of FIG. 7 is taken along the line 7,7 of FIG. 6, and the side elevational view of FIG. 8 is taken along the line 8,8 of FIG. 6.

The rolled resorbable membrane 101 in accordance with another embodiment of the present invention incorporates additional widows, such as for example, a first articular window 131 and a second articular window 151. As illustrated in FIG. 6, the first articular window 131 accommodates a left superior articular process 31 of the first vertebra 21, and the second articular window 151 accommodates a left superior articular process 51 of the second vertebra 23, respectively. The rolled resorbable membrane 101 is illustrated in FIG. 7 secured to the first vertebra 21 and the second vertebra 23 via only the first lateral window 125 and the second lateral window 145. FIG. 7 illustrates the rolled resorbable membrane 111 being secured to the first vertebra 21 and the second vertebra 23 via the first lateral window 125, the second lateral window 145, the first articular window 131 and the second articular window 151.

Portions of the left superior articular process 31 and the left superior articular process 51, which are adjacent with or protrude into the respective first articular window 131 and second articular window 151, are preferably decorticated in a manner similar to that discussed above in connection with the decortication of portions of the left transverse process 25 and the left transverse process 45. One or more of the first lateral window 125, second lateral window 135, first articular window 131 and second articular window 151 may be connected in modified embodiments of the present invention, as illustrated, for example, in FIG. 12, discussed infra. Vessels and associated cells will permeate through the rolled resorbable membrane 101 via the pores 149, and the portions of the windows 141, 151, to thereby promote the formation of bone within the protected space of the rolled resorbable membrane 101. When the rolled resorbable membrane 101 is eventually resorbed, a cylindrical bone formation fusing together the left superior articular process 31 and the left superior articular process 51 in accordance with the illustrated embodiment. The rolled resorbable membrane 111 is preferably formed in a similar way to promote fusion of the right superior articular process 33 of the first vertebra 21 to the right superior articular process 53 of the second vertebra 23.

The rolled resorbable membrane 101 may be supplied in a sterilized package with one or more of the windows, e.g., 125, 145, 131, 151, 205, 209, already formed therein, or may be supplied with no windows in which case the surgeon may cut the windows during the implant procedure using a mechanical or thermal cutting tool in vivo and/or in vitro. The windows may be formed to have rectangular, oval, or other shaped openings. Alternatively, the rolled resorbable membrane may be supplied in a sterile packaging with only miniature windows, e.g., half of the relative sizes shown, formed therein. The surgeon may then enlarge the windows in accordance with, for example, the sizes and locations of the transverse and superior articular processes. For example, as shown in FIG. 8, the first articular window 131 may be formed by the surgeon to be smaller than the second articular window 151 in accordance with a left superior articular process 31 decorticated portion that is smaller than a left superior articular process 51 decorticated portion.

In an embodiment wherein the seam, e.g., 110 or 212, is omitted altogether, the rolled resorbable membrane 101 can be constructed by providing a solid structure and forming a lumen (of constant or varying cross-sectional shape) therethrough; any windows (of constant or varying cross-sectional shape) can then be introduced as well. For example, in the case of a cylindrically-shaped, rolled resorbable membrane, the center of a solid cylinder of resorbable material is drilled out and, subsequently, windows and/or pores may optionally be introduced in the resulting rolled resorbable membrane. Alternatively, the rolled resorbable membrane may be injection or extrusion molded, with the windows and/or pores formed therein or subsequently added. A seam can be introduced in the resulting structure in other embodiments. In modified embodiments, a seam can be introduced into the resulting structure. The above-discussed drilled-out and other configurations of rolled resorbable membranes may be used in whole or in part with the other illustrated and discussed embodiments of the present invention. In addition, all combinations of the presently disclosed seam/windows/pores/membrane features of the preceding paragraphs which are not mutually inconsistent or incompatible are also included within the scope of the present invention.

Figure 9:
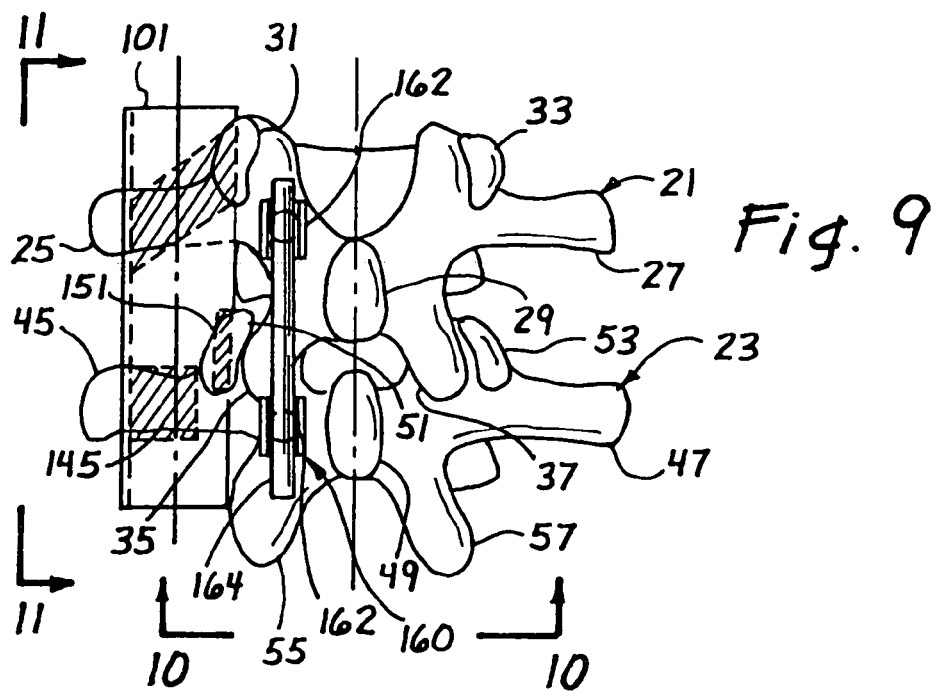
FIG. 9 illustrates a rigid fixation of the posterior lateral fusion configuration of FIGS. 6–8 in accordance with the present invention.
Figure 10:
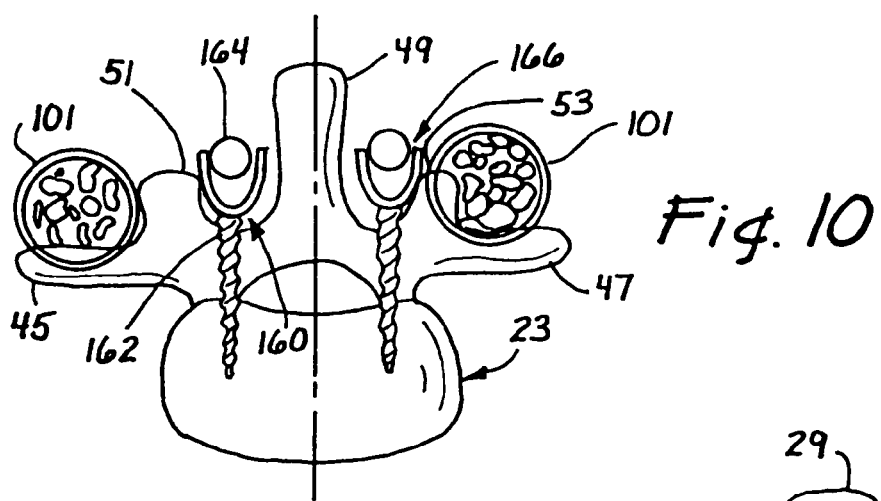
FIG. 10 is an end view of the rigidly-fixed posterior lateral fusion configuration of FIG. 9 in accordance with the present invention.
Figure 11:
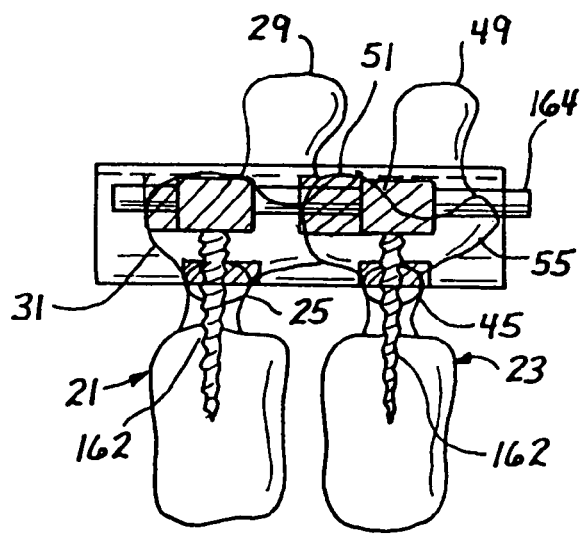
FIG. 11 is a side elevation view of the rigidly-fixed posterior lateral fusion configuration of FIG. 9 in accordance with the present invention.

Turning to FIGS. 9–11, the rolled resorbable membrane 101 is applied in combination with a fixation device 160, to the first vertebra 21 and the second vertebra 23. The fixation device 160 preferably comprises metallic screws, such as the cortical screws 162, and a metallic plate or rod, such as the rod 164. In modified embodiments, the fixation device may comprise resorbable screws and resorbable plates. The cortical screws 162 are secured to both the first vertebra 21 and the second vertebra 23, and the rod 164 is connected between the respective cortical screws 162. In alternative embodiments, resorbable or metallic tacks may be used in place of or in combination with the cortical screws 162. The fixation device 160, the cortical screws 162, and the rolled resorbable membrane 101 together hold the first vertebrae 21 and the second vertebrae 23 rigidly together for osteogenic fusion of the two vertebrae 21, 23. The space within the rolled resorbable membrane 101 is protected from any prolapse of adjacent soft tissues, for example, and is thus maintained for the formation and development of osteogenic tissue for posterior lateral fusion of the two vertebrae 21, 23. The fixation device 160 and the rolled resorbable membrane 101 may be used alone or in combination with another fixation device 166 (FIG. 10). FIG. 10 is an end view of the first vertebra 21 and the second vertebra 23, taken along the line 10, 10 of FIG. 9. FIG. 10 illustrates the rolled resorbable membrane 101 with another rolled resorbable membrane 111, and with both the of the fixation devices 160 and 166 rigidly securing the first vertebra 21 to the second vertebra 23. FIG. 11 is a side elevational view of the first vertebra 21 and the second vertebra 23, taken along the line 11, 11 of FIG. 9.

Figure 12:
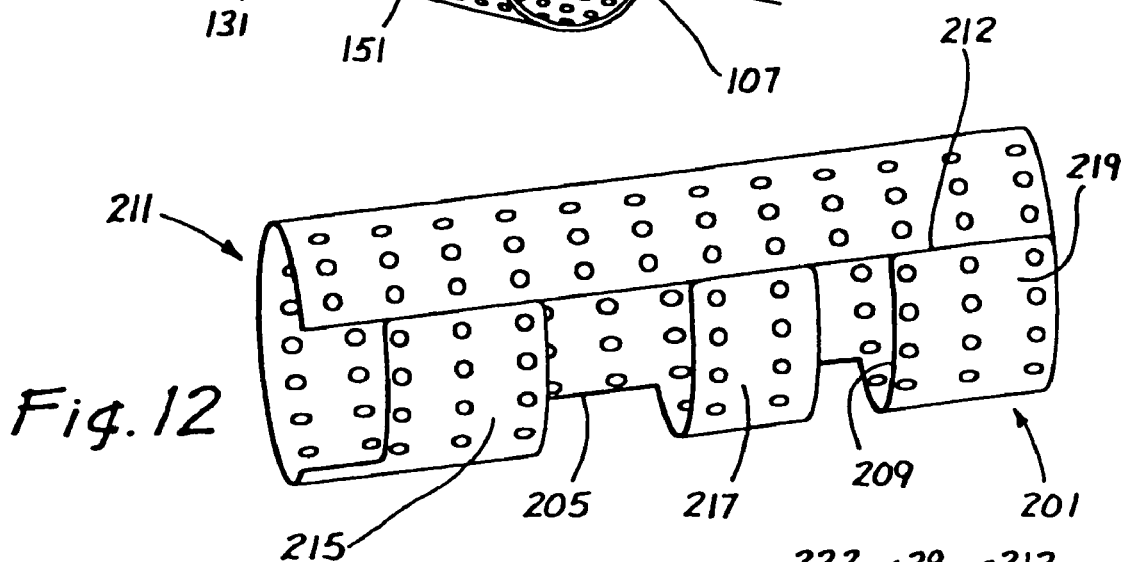
FIG. 12 illustrates a rolled resorbable membrane for facilitating posterior lateral fusion of two vertebrae in accordance with an alternative embodiment of the present invention.

FIG. 12 illustrates one implementation of an embodiment wherein at least one of the lateral and at least one of the articular windows are merged together to form one or more diagonal windows. A rolled resorbable membrane 201 is illustrated comprising a first diagonal window 205 and a second diagonal window 209. When a seam 212 is disposed adjacent to the first diagonal window 205 and the second diagonal window 209, three tabs 215, 217 and 219 are formed. In alternative embodiments, the seam may be disposed at other locations on the rolled resorbable membrane 201 in straight or non-straight form and extending continuously or partially along a length of the rolled resorbable membrane. In other modified embodiments comprising at least one diagonal window, the seam may be omitted altogether.

The combination of the rolled resorbable membrane 101 and the fixation device 160 may in some instances be constructed for operating together to relieve stress shielding within the protected space of the rolled resorbable membrane 101, to thereby prevent subsequent resorption of new bone. For example, the fixation device 160 may be installed with a slight looseness, may be constructed to be fully or partially resorbable, may be removed from the patient at a suitable time, or may be configured of a resorbable or partially resorbalbe material.

FIGS. 13–18 illustrate resorbable fixation devices for use with one or more rolled resorbable membranes to attenuate or eliminate stress shielding. In FIG. 13 a fixation device in the form of a resorbable fixation device 170 is illustrated connected to at least one of the first spinous process 29 and the second spinous process 49 with at least one fastening member, such as a screw 172. The resorbable fixation device 170 preferably comprises a thickness similar to that discussed above in connection with the rolled resorbable membrane, but may be formed to have greater thicknesses for added fixation strength. The resorbable fixation device 170 may be secured to the rolled resorbable membrane 101 by staples, rivets, tacks, screws, or heat welding, but is preferably integrally formed with the rolled resorbable membrane 101. The resorbable fixation device 170 may be configured to secure only the rolled resorbable membrane 101 to the first spinous process 29, or may be configured to secure both the rolled resorbable membrane 101 and the rolled resorbable membrane 111 to the first spinous process 29 in which case the resorbable fixation device 170 preferably extends over and is secured to both sides of the first spinous process 29 with screws 172. In one preferred embodiment, a single sheet of base material, having pores as discussed above, is used to form the resorbable fixation device and the at least one rolled resorbable membrane. In another preferred embodiment, the resorbable fixation device 170 is formed without pores for added fixation strength. A side elevational view of the configuration of FIG. 13, taken along the line 14, 14 of FIG. 13, is shown in FIG. 14. The resorbable fixation device 170 of FIG. 14 does not extend along the length of the resorbable fixation device 170, but rather in the illustrated embodiment extends a length sufficient to facilitate adequate attachment to the first spinous process 29. In other embodiments, the resorbable fixation device 170 may be formed to extend further along the length of the rolled resorbable membrane 170, as shown in phantom at 171, to facilitate attachment thereof to both the first spinous process 29 and the second spinous process 49. In another embodiment, the resorbable fixation device 170 may be formed to extend still further along the length of the rolled resorbable membrane 170, as shown in phantom at 173, to facilitate attachment thereof to both the first spinous process 29, the second spinous process 49, and the spinous process 175 of an adjacent vertebra (not shown). Other shapes and configurations of the resorbable fixation device are also contemplated.

In FIG. 15 a fixation device in the form of a resorbable fixation device 180 is illustrated connected to at least one of the first spinous process 29 and the second spinous process 49 with at least one fastening member, such as a screw 182. A side elevational view, taken along the line 16, 16 of FIG. 15, is shown in FIG. 16. The resorbable fixation device 180 preferably comprises a thickness similar to that discussed above in connection with the rolled resorbable membrane, but may be formed to have greater thicknesses for added fixation strength. The resorbable fixation device 180 may be secured to the rolled resorbable membrane 101a by staples, rivets, tacks, screws, or heat welding, but is preferably integrally formed with the rolled resorbable membrane 101a. The resorbable fixation device 180 may be configured to secure only the rolled resorbable membrane 101a to the first spinous process 29, or as presently embodied, is configured to secure both the rolled resorbable membrane 101a and the rolled resorbable membrane 111a to the first spinous process 29 in which case the resorbable fixation device 180 preferably extends over and is secured to both sides of the first spinous process 29 with screws 182. Alternatively, the resorbable fixation device 180 may comprise two separate pieces, each of which terminates near the top of the first spinous process 29, as distinguished from the resorbable fixation device comprising a single piece which extends over the first spinous process 29.

In a preferred embodiment, a single sheet of base material, having pores as discussed above, is used to form the resorbable fixation device 180 and the two rolled resorbable membranes 101a, 111a. In one such integral embodiment, the resorbable fixation device 180 can be formed without pores for added fixation strength while the two rolled resorbable membranes 101a, 111a are formed with pores. Windows may be formed, such as for example the windows formed in the rolled resorbable membrane 101a as shown in FIGS. 15 and 16 or, alternatively, the rolled resorbable membrane may be formed with diagonal windows, such as shown in FIG. 12. In other embodiments, the rolled resorbable membrane may be formed with articular windows, lateral windows and/or diagonal windows.

In an embodiment wherein a single sheet of base material is used to form the resorbable fixation device 180 and the two rolled resorbable membranes 101a, 111a, the base material may be provided in a planar shape. It may then be preformed to approximate the bends shown in FIGS. 15 and 16, or may be implanted in a planar form and bent and held by fasteners. For example, an end of the base material which will be used to form the rolled resorbable membrane 101a can be secured to at least one of the left transverse process 25 and the left transverse process 45 with at least one resorbable fastener, such as a screw or tack 185. Windows 186 and 187 may then be fitted over the left superior articular process 31 and the left superior articular process 51. The base material may then be formed over and secured to at least one of the first spinous process 29 and the second spinous process 49. In the illustrated embodiment, the resorbable fixation device 180 is fitted and secured to only the first spinous process 29. However, in a modified embodiment the resorbable fixation device 180 is formed to fit over and be secured to both the first spinous process 29 and the second spinous process 49. In another embodiment, the resorbable fixation device 180 may be formed as shown in phantom at 181 in FIG. 16, to fit over and be secured to only the second spinous process 49. In yet another embodiment where added strength is desired, the base material is extended from the second-spinous-process portion 181 to a third-spinous-process portion 183 for attachment to a spinous process 175 of an adjacent vertebra 175. The base material is then fitted over the right superior articular processes 33, 53 and the right transverse processes 27, 47 with any of four corresponding window being disposed in the resorbable fixation device for accommodating any of the four spinous elements 33, 53, 27 and 47. In the illustrated embodiment, windows are formed to accommodate the right transverse processes 27 and 47, and the resorbable fixation device 180 is secured to the right superior articular processes 33, 53, with resorbable fasteners, such as a screw or tack 188. The opposing ends of the resorbable fixation device 180 may then be folded over and secured to the corresponding superior articular processes 31, 33, 51, 53, and/or the resorbable fixation device 180 and/or the corresponding spinous processes 29, 49, to thereby form the rolled resorbable membranes 101a and 111a. Bone grafts, bone graft substitutes, growth factor elements and/or other items can be placed into the rolled resorbable membranes 101a and 111a before, after or during the folding and securing steps. As shown in FIGS. 15 and 16, the rolled resorbable membrane 101a is formed by securing an end of the resorbable fixation device 180 to the left superior articular processes 31, 51 with resorbable fasteners, such as a screw or tack 189, and the rolled resorbable membrane 111a is formed by securing an end of the resorbable fixation device 180 to the right superior articular processes 33, 53 with resorbable fasteners, such as a screw or tack 188. When each resorbable fasteners 188 is used to extend through both layers of the resorbable fixation device and into a corresponding superior articular process, the earlier step of securing the resorbable fasteners 188 may be omitted. Optional sutures or staples 190 may be used alone or in combination with the resorbable fasteners 188. The overlapping of the resorbable fixation device then preferably terminates near the spinous processes, but in modified embodiments may be configured to extend (and overlap over itself) back over the spinous processes as well for added strength in which case the overlapping portions are secured with the same or additional resorbable fasteners 182 or 182a.

Figure 17:
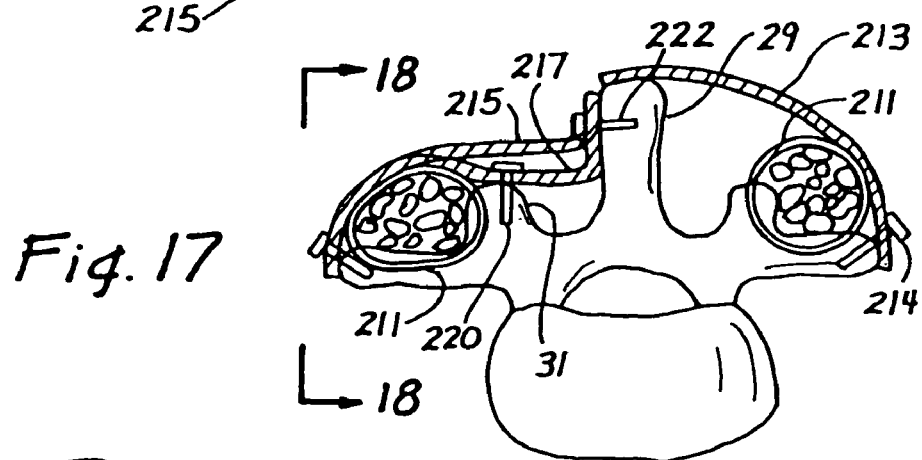
FIG. 17 illustrates resorbable membranes placed onto two vertebrae for facilitating posterior lateral fusion of the vertebrae in accordance other alternative embodiments of the present invention.
Figure 18:
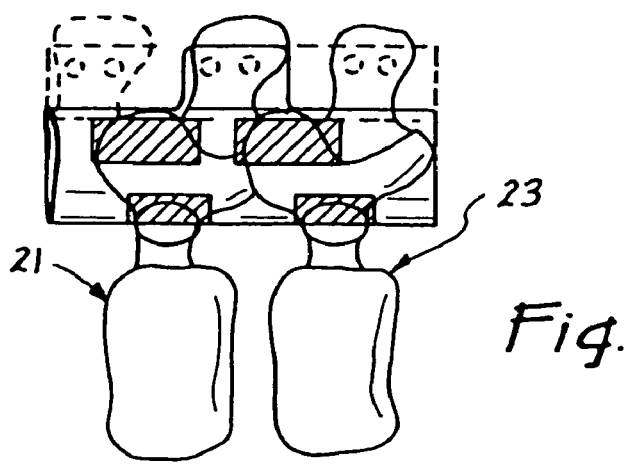
FIG. 18 is a side elevation view of the posterior lateral fusion configuration of FIG. 17 in accordance with the present invention.

FIGS. 17 and 18 illustrate another embodiment wherein a fixation device is used in combination with a resorbable membrane 211. FIG. 18 is a side elevational view, taken along the line 18, 18 of FIG. 18. The fixation device is first placed in a position 213 and optionally secured with at least one optional resorbable fastener 214. One or more rolled resorbable membranes 211 are the positioned, and the fixation device is then positioned over the rolled resorbable membrane 211 to contact the spinous process 29, as shown by the position 213. The rolled resorbable membrane is then moved to the position 215 and, subsequently, moved to the position 217 where optional fasteners 220 and 222 optionally may be secured into the left superior articular process 31 and the spinous process 29, respectively.

As presently embodied, the period of time sufficient for complete new bone regeneration within the protected space of the rolled resorbable membrane 101 is between approximately 2 to 24 months. Thus, according to the present invention, the resorption of the rolled resorbable membranes 101, 111 and the resorbable fixation devices to a point where they can no longer shield any mechanical stresses is between approximately 2 and 24 months. Moreover, due to the construction and positioning of the rolled resorbable membranes 101, 111, and the resorbable fixation devices it would not be likely that substantial stress shielding would occur to the fusion site. This is of course especially true after the implants begin to lose their strength during the resorption process. The rolled resorbable membranes and resorbable fixation devices of the presently preferred embodiment are preferably resorbed within the body of the patient to a point where substantial rigidity is no longer present within a period of approximately 1 year. Complete resorption of the rolled resorbable membrane may subsequently occur after a total period of 1.5 to 2 years has elapsed since the initial implantation. In other embodiments, one or both of the rolled resorbable membranes 101 and 111, and or any of the above-discussed fixation devices, may comprise a non-resorbable plastic or metallic materials.

Although an exemplary embodiment of the invention has been shown and described, many other changes, modifications and substitutions, in addition to those set forth in the above paragraphs, may be made by one having ordinary skill in the art without necessarily departing from the spirit and scope of this invention.

The invention claimed is:

1. An implant, comprising:
    a membrane of resorbable polymer base material having a first side, a second side, a thickness measured between the first side and the second side ranging from about 0.5 mm to about 3 mm, and a perimeter edge joining the first side to the second side, wherein first and second points are disposed on opposing sides of the perimeter edge, the membrane of resorbable polymer base material being adapted to be rolled to bring the first point into proximity with the second point to thereby form a rolled membrane of resorbable polymer base material;
    a plurality or apertures disposed in the membrane of resorbable polymer base material, the plurality of apertures being substantially distributed over at least a portion of both the first side and the second side of the membrane of resorbable polymer base material, apertures of the plurality of apertures having widths ranging from about 500 microns to about 3000 microns and defining fluid-flow paths from the first side to the second side; and
    a window formed in the membrane of resorbable polymer base material, the window having a dimension greater than about 5 mm.

2. The implant as set forth in claim 1, wherein the implant is sealed in a sterile package.

3. The implant as set forth in claim 1, wherein the window comprises a width greater than about 6 mm and a length greater than about 11 mm.

4. The implant as set forth in claim 3, wherein:
    the implant is adapted to contain a bone-graft or growth material and to facilitate posterior lateral fusion of at least two vertebrae following an in vivo surgical procedure; and
    the window is sized and shaped to accommodate a portion of a transverse process of one of the two vertebrae into the rolled membrane of resorbable polymer base material when the rolled membrane of resorbable polymer base material is placed into contact with the at least two vertebrae.

5. The implant as set forth in claim 4, wherein the window is further sized and shaped to accommodate a portion of a superior articular process of one of the two vertebrae when the membrane of resorbable polymer base material is rolled and placed into contact with the at least two vertebrae.

6. The implant for as set forth in claim 5, wherein the membrane of resorbable polymer base material has a rectangular perimeter edge and the window has an edge which is not parallel to any of the four edges of the rectangular perimeter edge.

7. The implant as set forth in claim 1, wherein:
    the implant is adapted to contain a bone-graft or growth material and to facilitate posterior lateral fusion of at least two vertebrae following an in vivo surgical procedure;
    the window comprises a first window which is sized and shaped, when the membrane of resorbable polymer base material is rolled and placed into contact with the at least two vertebrae, to accommodate both a portion of a transverse process of one of the two vertebrae and a portion of a superior articular process of one of the two vertebrae; and the implant comprises a second window which is sized and shaped, when the membrane of resorbable polymer base material is rolled and placed into contact with the at least two vertebrae, to accommodate both a portion of a transverse process of the other of the two vertebrae and a portion of a superior articular process of the other of the two vertebrae.

8. The implant as set forth in claim 1, wherein:

the implant is adapted to contain a bone-graft or growth material and to facilitate posterior lateral fusion of at least two vertebrae following an in vivo surgical procedure;

the window comprises an articular first window which is sized and shaped, when the membrane of resorbable polymer base material is rolled and placed into contact with the at least two vertebrae, to accommodate a portion of a superior articular process of one of the two vertebrae;

the implant comprises a transverse first window which is sized and shaped, when the membrane of resorbable polymer base material is rolled and placed into contact with the at least two vertebrae, to accommodate a portion of a transverse process of one of the two vertebrae;

the window comprises an articular second window which is sized and shaped, when the membrane of resorbable polymer base material is rolled and placed into contact with the at least two vertebrae, to accommodate a portion of a superior articular process of the other of the two vertebrae; and the implant comprises a transverse second window which is sized and shaped, when the membrane of resorbable polymer base material is rolled and placed into contact with the at least two vertebrae, to accommodate a portion of a transverse process of the other of the two vertebrae.

9. The implant as set forth in claim 8, wherein the implant further comprises an articular third window which is sized and shaped, when the membrane of resorbable polymer base material is rolled and placed into contact with the at least two vertebrae, to accommodate a portion of a superior articular process of a third vertebrae.

10. An implant for containing a bone-graft or growth material and facilitating posterior lateral fusion of at least two vertebrae following an in vivo surgical procedure, the implant comprising:

a membrane of polymer base material having a first side, a second side, and a perimeter edge joining the first side to the second side, wherein first and second points are disposed on opposing sides of the perimeter edge, the membrane of polymer base material being adapted to be rolled to bring the first point into proximity with the second point to thereby form a rolled membrane of polymer base material; and a window formed in the membrane of polymer base material, the window having a width that is greater than about 5 mm, the window being sized and shaped to accommodate a portion of a transverse process of one of the two vertebrae into the rolled membrane of polymer base material when the rolled membrane of polymer base material is placed into contact with the at least two vertebrae.

11. The implant for containing a bone-graft material and facilitating posterior lateral fusion as set forth in claim 10, wherein the membrane of polymer base material is non-porous.

12. The implant for containing a bone-graft material and facilitating posterior lateral fusion as set forth in claim 10, wherein the polymer is a resorbable polymer.

13. The implant for containing a bone-graft material and facilitating posterior lateral fusion as set forth in claim 12, wherein the membrane of polymer base material is non-porous.

14. The implant for containing a bone-graft material and facilitating posterior lateral fusion as set forth in claim 12, wherein the implant further comprises a plurality or apertures disposed in the membrane of polymer base material, the plurality of apertures being substantially uniformly distributed over at least a portion of both the first side and the second side of the membrane of polymer base material, each of the plurality of apertures of the implant having a width which is between about 500 microns and about 3000 microns and which defines an isolated, non-intersecting, fluid-flow path from the first side to the second side, wherein each of the plurality of apertures of the membrane of polymer base material immediately after implanting of the membrane of polymer base material, has a diameter sufficient in size to prevent gross prolapse of adjacent soft tissues into a center of the rolled membrane of resorbable polymer base material and to allow a proliferation of vasculature and connective tissue cells, derived from adjacent soft tissues, to permeate through the aperture and substantially into a center of the rolled membrane of polymer base material.

15. The implant for containing a bone-graft material and facilitating posterior lateral fusion as set forth in claim 10, wherein the implant is sealed in a sterile package.

16. The implant for containing a bone-graft material and facilitating posterior lateral fusion as set forth in claim 10, wherein the window comprises a width greater than about 6 mm and a length greater than about 11 mm.

17. The implant for containing a bone-graft material and facilitating posterior lateral fusion as set forth in claim 16, wherein the window is further sized and shaped to accommodate a portion of a superior articular process of one of the two vertebrae when the membrane of polymer base material is rolled and placed into contact with the at least two vertebrae.

18. The implant for containing a bone-graft material and facilitating posterior lateral fusion as set forth in claim 17, wherein the membrane of polymer base material has a rectangular perimeter edge and the window comprises an edge which is not parallel to any of the four edges of the rectangular perimeter edge.

19. The implant for containing a bone-graft material and facilitating posterior lateral fusion as set forth in claim 10, wherein:

the window comprises a first window which is sized and shaped, when the membrane of polymer base material is rolled and placed into contact with the at least two vertebrae, to accommodate both a portion of a transverse process of one of the two vertebrae and a portion of a superior articular process of one of the two vertebrae; and the implant comprises a second window which is sized and shaped, when the membrane of polymer base material is rolled and placed into contact with the at least two vertebrae, to accommodate both a portion of a transverse process of the other of the two vertebrae and a portion of a superior articular process of the other of the two vertebrae.

20. The implant for containing a bone-graft material and facilitating posterior lateral fusion as set forth in claim 10, wherein:
the window comprises an articular first window which is sized and shaped, when the membrane of polymer base material is rolled and placed into contact with the at least two vertebrae, to accommodate a portion of a superior articular process of one of the two vertebrae;
the implant comprises a transverse first window which is sized and shaped, when the membrane of polymer base material is rolled and placed into contact with the at least two vertebrae, to accommodate a portion of a transverse process of one of the two vertebrae;
the window comprises an articular second window which is sized and shaped, when the membrane of polymer base material is rolled and placed into contact with the at least two vertebrae, to accommodate a portion of a superior articular process of the other of the two vertebrae; and
the implant comprises a transverse second window which is sized and shaped, when the membrane of polymer base material is rolled and placed into contact with the at least two vertebrae, to accommodate a portion of a transverse process of the other of the two vertebrae.

21. The implant for containing a bone-graft material and facilitating posterior lateral fusion as set forth in claim 20, wherein:
the polymer is a resorbable polymer; and
the implant further comprises an articular third window which is sized and shaped, when the membrane of polymer base material is rolled and placed into contact with the at least two vertebrae, to accommodate a portion of a superior articular process of a third vertebrae.

22. The implant for containing a bone-graft material and facilitating posterior lateral fusion as set forth in claim 10, wherein the implant further comprises a plurality or apertures disposed in the membrane of polymer base material, the plurality of apertures being substantially uniformly distributed over at least a portion of both the first side and the second side of the membrane of polymer base material, each of the plurality of apertures of the implant having a width which is less than about 40 microns and which defines an isolated, non-intersecting, fluid-flow path from the first side to the second side.

23. The implant for containing a bone-graft material and facilitating posterior lateral fusion as set forth in claim 10, wherein a thickness of the membrane of polymer base material, measured between the first side and the second side, ranges from about 0.5 mm to about 3 mm.

* * * * *